(12) United States Patent
Guchelaar et al.

(10) Patent No.: US 8,029,998 B2
(45) Date of Patent: Oct. 4, 2011

(54) GENETIC MARKERS FOR PROGNOSIS OF ANTIFOLATE TREATMENT EFFICACY

(75) Inventors: Hendrik Jan Guchelaar, Gouda (NL); Tom Willem Johannes Huizinga, Leiden (NL)

(73) Assignee: Academisch Ziekenhuis Leiden H.O.D.N. LUMC, Leiden (NL)

( * ) Notice: Subject to any disclaimer, the term of this patent is extended or adjusted under 35 U.S.C. 154(b) by 268 days.

(21) Appl. No.: 12/184,184

(22) Filed: Jul. 31, 2008

(65) Prior Publication Data

US 2009/0029379 A1 Jan. 29, 2009

Related U.S. Application Data

(62) Division of application No. 11/400,232, filed on Apr. 10, 2006, now Pat. No. 7,713,696.

(51) Int. Cl.
*C12Q 1/68* (2006.01)
*C12P 19/34* (2006.01)

(52) U.S. Cl. ...... 435/6.1; 435/6.11; 435/6.13; 435/6.18; 435/91.1; 436/63

(58) Field of Classification Search .................. None
See application file for complete search history.

(56) References Cited

U.S. PATENT DOCUMENTS

| 7,702,469 B2 | 4/2010 | Huizinga et al. |
| 7,713,696 B2 | 5/2010 | Guchelaar et al. |
| 2007/0238103 A1 | 10/2007 | Guchelaar et al. |
| 2008/0288177 A1 | 11/2008 | Guchelaar et al. |
| 2010/0240541 A1 | 9/2010 | Guchelaar et al. |

OTHER PUBLICATIONS

AMPD1 Gene, Adenosine monophosphate deaminase 1 gene, pp. 1-16, available at genecards.org, printed Aug. 13, 2008.
Alethaha et al., Remission and Active Disease in Rheumatoid Arthritis, Defining Criteria for Disease Activity Status, Arthritis & Rheumatism, vol. 52, No. 9, 2625-2636, (2005).
Alethaha et al., The Rheumatoid Arthritis Patient in the Clinic: Comparing more than 1300 Consecutive DMARD Courses, Rheumatology, vol. 41, 1367-1374, (2002).
Anderson et al., Factors Predicting Response to Treatment in Rheumatoid Arthritis, Arthritis & Rheumatism, vol. 43 No. 1, 22-29, (2000).
Bosco et al., Methionine Synthase (MTR) 2756 (A→G) Polymorphism, Double Heterozygosity Methionine Synthase 2756/AG Methionine Synthase Reductase (MTRR) 66 AG, and Elevated Homocysteinemia Are Three Factors for Having a Child with Down Syndrome, American Journal of Medical Genetics, vol. 121A, 219-224, (2003).
Bulock et al., The Kinetic Mechanism of the Human Bifunctional Enzyme 5-Aminoimidazole-Carboxamide Ribonucleotide Formyltransferase/Inosince 5'—Monophosphate Cyclohydrolase: A Surprising Lack of Substate Channeling, The Journal of Biological Chemistry, vol. 277 No. 25, 22168-22174, (2002).
Cao et al., DNA Polymorphisms in ITPA including basis of inosine triphosphatease deficiency, J Hum Genet, vol. 47, 620-622, (2002).
Chan et al. Molecular Action of Methotrexate in inflammatory Diseases, Arthritis Research, vol. 4, No. 4, 266-273, 2002.
Cronstein et al., Methotrexate inhibits Neutrophil Function by Stimulating Adenosine Release from Connective Tissue Cells, Proc. Natl. Acad. Sci. USA, vol. 88, 2441-2445, (1991).
Cronstein, Low-Dose Methotrexate: A Mainstay in the Treatment of Rheumatoid Arthritis, Pharmacological Reviews, vol. 57, No. 2, 163-172, (2005).
Cutolo et al., Anti-inflammatory Mechanisms of Methotrexate in Rheumatoid Arthritis, Annals of the Rheumatic Diseases, vol. 60, 729-735, (2001).
Delano et al., Genetically Based Resistance to the Anti-inflammatory Effects of Methotrexate in the Air-Pouch Model of Acute Inflammation, Arthritis & Rheumatism, vol. 52, No. 8, 2567-2575, (2005).
Dervieux et al., Polyglutamation of Methotrexate with common Polymorphisms in reduced folate carrier, Aminoimidazole carboxamide ribonucleotide transformylase, and thymidylate synthase are associated with methotrexate effects in rheumatoid arthritis, Arthritis & Rheumatism, vol. 50, No. 9, 2766-2774, (2004).
Evans et al., Pharmacogenomics—Drug Disposition, Drug Targets, and Side Effects, The New England Journal of Medicine, vol. 348, No. 6, 538-549, (2003).
Gaughan et al., The Methionine Synthase Reductase (MTRR) A66G Polymporphism is a novel genetic determinant of plasma homocysteine concentrations, Atheroslerosis, vol. 157, 451-456, (2001).
GeneCards, Adenoise monophosphate deaminase 1 (isoform M) pp. 1-16, available at genecards.org., printed Aug. 2008.
Genovese et al., Etanercept Versus Methotrexate in Patients with Early Rheumatoid Arthritis, Arthritis & Rheumatism, vol. 46 No. 6, 1443-1450, (2002).
Goekoop-Ruiterman et al., Clinical and Radiographic Outcomes of Four Different Treatment Strategies in Patients with Early Rheumatoid Arthritis (the BeSt Study), a Randomized, Controlled Trial, Arthritis & Rheumatism, vol. 52, No. 11, 3381-3390, (2005).
Gossec et al., Prognostic factors for remission in early rheumatoid arthritis: a multiparameter prospective study, Annals of the Rheumatic Diseases, vol. 63, 675-680, (2004).
Hattersley et al., Genetic Epidemiology. 5, What makes a good genetic association study? The Lancet, vol. 366, 1315-1323, (2005).
Hider, S.L., et al., The Pharmacogenetics of Methotrexate, Rheumatology, 2007, 46: 1520-1524.
Huizinga et al., Associations, Populations, and the Truth, Arthritis & Rheumatism, vol. 50, No. 7, 2066-2071, (2004).
Ioannidis et al., Replication Validity of Genetic Association Studies, Nature Genetics, vol. 29, 306-309, (2001).

(Continued)

*Primary Examiner* — Sarae Bausch
(74) *Attorney, Agent, or Firm* — McDonnell Boehnen Hulbert & Berghoff LLP

(57) ABSTRACT

Methods and kits for predicting the efficacy of antifolate (e.g., methotrexate) treatment of rheumatoid arthritis by detecting polymorphisms, particularly single nucleotide polymorphisms, in adenosine pathway genes.

6 Claims, 3 Drawing Sheets

OTHER PUBLICATIONS

Israel et al., Use of Regularly Scheduled Albuterol Treatment in Asthma: Genotype-Stratified, Randomised, Placebo-controlled cross-over trial, The Lancet, vol. 364, 1505-1512, (2004).

Kalsi et al., Decreased Cardiac Activity of AMP Deaminase in Subjects with the AMPD1 Mutation—A potential Mechanism of Protection in heart failure, Cardiovascular Research, vol. 59, 678-684, (2003).

Klareskog et al., Therapeutic effect of the combination of etanercept and methotrexate compared with each treatment alone in patients with rheumatoid arthritis: double-blind randomized controlled trial, The Lancet, vol. 363, 675-681, (2004).

Lucia, et al., "C34T mutation of the AMPD1 gene in an elite white runner", Br J Sports Med, 2006 vol. e7, pp. 1-3.

Marinaki et al., Adverse Drug Reactions to Azathioprine Therapy are Associated with Polymorphism in the Gene Encoding Inosine Triphosphate Pyrophosphatase (ITPase), Pharmacogenetics, vol. 14, No. 3, 181-187, (2004).

Matteson et al., How Aggressive Should Initial Therapy for Rheumatoid Arthritis be? Factors Associated with Response to 'non-aggressive' DMARD Treatment and Perspective from a two-year Open Label Trial, Rheumatology, vol. 43, 619-625, (2004).

Montesinos et al., Adenosine $A_{2a}$ or $A_3$ Receptors are Required for Inhibition of Inflammation by Methotrexate and Its Analog MX-68, Arthritis & Rheumatism, vol. 48, No. 1, 240-247, (2003).

Morabito et al., Methotrexate and Sulfasalazine Promote Adenosine Release by a Mechanism that Requires Ecto-5-Nucleotidase-mediated Conversion of Adenine Neucleotides, J. Clinical Investigation, vol. 101, No. 2, 295-300, (1998).

Morisaki et al., Molecular basis of AMP Deaminase Deficiency in Skeletal Muscle, Proc. Natl. Acad. Sci. USA, vol. 89, 6457-6461, (1992).

Mottonen et al., Comparison of Combination Therapy with Single-Drug Therapy in Early Rheumatoid Arthritis: A Randomised Trial, The Lancet, vol. 353, 1568-1573, (1999).

Mummidi, et al., J. Biological Chemistry, 2000, vol. 275, pp. 18946-18961.

Nakamachi et al., Specific Increase in Enxymatic Activity of Adenosine Deaminase 1 in Rheumatoid Synovial Fibroblasts, Arthritis and Rheumatism, vol. 48., No. 3, 668-674, (2003).

Netwon-Cheh et al., Genetic Association Studies of Complex Traits: Design and Analysis Issues, Mutation Research, vol. 573, 54-69, (2005).

O'Dell et al., Treatment of Rheumatoid Arthritis with Methotrexate Alone, Sulfasalzine and Hydroxychloroquine, or a Combination of all three Medications, New Engl. J. Med., vol. 334, No. 20, 1287-1291, (1996).

Pepe et al., Am. J. Epidemiology 159:882-890 (2004).

Pincus et al., Methotrexate as the "anchor drug" for the treatment of early rheumatoid arthritis, Clinical and Experimental Rheumatology, vol. 21, Suppl. 31, S179-S185, (2003).

Pincus, Long-Term Outcomes in Rheumatoid Arthritis, British Journal of Rheumatology, vol. 34 Suppl. 2, 59-73, (1995).

Puolakka et al., Early Suppression of Disease Activity is Essential for Maintenance of Work Capacity in Patients with Recent-Onset Rheumatoid Arthritis, Arthritis & Rheumatism, vol. 52, No. 1, 36-41, (2005).

Riksen et al, Arthritis Rheum., Letters, 2006, pp. 694-695.

Rocha et al., Pharmacogenetics of outcome in children with acute lymphoblastic leukemia, Blood, vol. 105, 4752-4758, (2005).

Smolen et al., Therapeutic Strategies in early Rheumatoid Arthritis, Best Practice & Research Clinical Rheumatology, vol. 19, No. 1, 163-177, (2005).

Urano et al., Polymorphisms in the methylenetetrahdrofolate reductase, gene were associated with both the efficacy and the toxicity of methotrexate used for the treatment of rheumatoid arthritis, as evidence by single locus and haplotype analyses, Pharmacogenetics, vol. 12, 183-190, (2002).

Van Der Heijde et al., Development of a Disease Activity Score Based on Judgment in Clinical Practice by Rheumatologists, The Journal of Rheumatology, vol. 20, No. 3, 579-581, (1993).

Van Gestel et al., Development and Validation of the European League against Rheumatism Response Criteria for Rheumatoid Arthritis, Arthritis & Rheumatism, vol. 39. No. 1, 34-40 (1996).

Verstappen et al., A good response to early DMARD treatment of patients of rheumatoid arthritis in the first year predicts remission during follow-up, Annals of the Rheumatic Diseases, 1-17, (May 6, 2004).

Verstappen et al., Five-Year Follow up of Rheumatoid Arthritis Patients After Early Treatment with Disease-Modifying Antirheumatic Drugs Versus Treatment According to the Pyramid Approach in the First Year, Arthritis & Rheumatism, vol. 48 No. 7, 1797-1807, (2003).

Wessels et al., Efficacy and Toxicity of Methotrexate in Early Rheumatoid Arthritis Are Associated with Single-Nucleotide Polymorphisms in Genes Coding for Folate Pathway Enzymes, Arthritis & Rheumatism, vol. 54, No. 4 1087-1095, (2006).

GENETIC MARKERS FOR PROGNOSIS OF ANTIFOLATE TREATMENT EFFICACY

FIELD OF THE INVENTION

The current invention relates to the field of medicine, in particular the fields of rheumatoid arthritis and genetic diagnostics

BACKGROUND OF THE INVENTION

Rheumatoid arthritis (RA) patients differ considerably in their clinical course and in response to treatment (1; 2). Despite the fact that studies are supporting combination therapy to optimally suppress disease activity, most newly diagnosed patients start with monotherapy, with the antifolate methotrexate (MTX) being the preferred disease-modifying antirheumatic drug (DMARD) (3-6).

Randomized controlled clinical trials provide evidence that methotrexate alters the clinical course, although only about 40% of the patients show good clinical response (7-9). On the other hand, lack of response is associated with progression of joint damage and functional decline (6; 10; 11). However, it is not possible to predict which patients will respond since most studies concerning methotrexate efficacy have not investigated the predictors for response. Clear predictors for response to methotrexate will contribute to the allocation of effective therapy and will establish the reduction of disease activity and limit functional decline.

In candidate gene driven pharmacogenetic studies, polymorphisms in genes coding for proteins involved in pharmacokinetic or pharmacodynamic pathways related to the drug under study are selected and tested for associations with treatment outcome (12-14). For methotrexate, several studies showed that single nucleotide polymorphisms in genes coding for the folate pathway enzymes are associated with treatment response (15-17). Although methotrexate may act in rheumatoid arthritis through inhibition of folate pathway enzymes, more recent reports indicate that its response may also be related to the release of endogenous anti-inflammatory adenosine (18; 19). Studies concerning other complex traits have indicated the relevance of polymorphisms in genes coding for enzymes related to adenosine release for clinical outcome (15; 20-24). The current invention demonstrates for the first time that genetic variants in these genes are associated with methotrexate treatment outcome and exploits these associations for methods of diagnostics and treatment.

SUMMARY OF THE INVENTION

The present invention provides a correlation of specific allelic variants in genes related to and/or involved in adenosine metabolism to antifolate (e.g., methotrexate) treatment response in rheumatoid arthritis patients. The association of allelic variants and MTX response is of particular relevance to patients with recent-onset RA, and may be used as a diagnostic and/or prognostic tool. Patients having a genetic profile associated with a positive response to MTX treatment may be preferentially treated with the recommended dose of MTX. Patients having a genetic profile rendering them refractory to methotrexate treatment may be preferentially treated with one or more alternative DMARDs. The different alleles for genes and gene products in the adenosine release pathway can be identified using any available technique for the identification of gene sequences, expression profiles and genetic polymorphisms.

One embodiment of the present invention is a method for determining clinical responsiveness to antifolate therapy in a mammal afflicted with, or at risk of developing, rheumatoid arthritis, by identifying a polymorphism in the adenosine monophosphate deaminase (AMPD1) gene, wherein the presence of the single nucleotide polymorphism is indicative of clinical responsiveness to the antifolate therapy. The antifolate may be methotrexate. In one embodiment, the polymorphism is a single nucleotide polymorphism. In another embodiment, the single nucleotide polymorphism is 34C>T.

Another embodiment is a method for determining clinical responsiveness to antifolate therapy in a mammal afflicted with, or at risk of developing, rheumatoid arthritis, by identifying a polymorphism in the inosine triphosphate pyrophosphatase (ITPA) gene, wherein the presence of the single nucleotide polymorphism is indicative of clinical responsiveness to the antifolate therapy. The antifolate may be methotrexate. In one embodiment, the polymorphism is a single nucleotide polymorphism. In another embodiment, the single nucleotide polymorphism is 94A>C.

The present invention also provides a method for determining clinical responsiveness to antifolate therapy in a mammal afflicted with, or at risk of developing, rheumatoid arthritis by determining the presence of a polymorphism in at least two of the following genes: adenosine monophosphate deaminate (AMPD1), aminoimidazole carboxamide ribonucleotide transformylase (ATIC), inosine triphosphate pyrophosphatase (ITPA), methionine synthase (MTR) and methionine synthase reductase (MTRR). In one embodiment, the gene is AMPD, ATIC or ITPA, wherein the presence of the single nucleotide polymorphism is indicative of clinical responsiveness to the antifolate therapy. The antifolate may be methotrexate. In one embodiment, the polymorphism is a single nucleotide polymorphism. In one aspect of this embodiment, the single nucleotide polymorphism is AMPD1 34C>T, ATIC 347 C>G or ITPA 94A>C. The single nucleotide polymorphisms may be one of the following combinations: AMPD1 34C>T and ATIC 347 CC; AMPD1 34C>T and ITPA 94CC; or ATIC 347CC and ITPA 94CC. In another embodiment, the single nucleotide polymorphism is AMPD1 34 C>T, ATIC 347 C>G and ITPA 94A>C. In one embodiment, antifolate responsiveness is measured as a disease activity score (DAS) #2.4. In one aspect, the mammal is a human.

In one embodiment, in any of the methods described above, the polymorphism is detected by microarray analysis, DNA sequencing or allele specific PCR techniques.

The present invention also provides a kit of parts comprising at least one oligonucleotide capable of hybridizing to, or adjacent to, a polymorphic site in a DNA sequence present in the AMPD1 gene.

Another embodiment of the present invention is a kit of parts comprising at least one oligonucleotide capable of hybridizing to, or adjacent to, a polymorphic site in a DNA sequence present in the ITPA gene.

The present invention also provides a kit of parts comprising at least two oligonucleotides capable of hybridizing to, or adjacent to, a polymorphic site in a DNA sequence present in at least two of the following genes: adenosine monophosphate deaminate (AMPD1), aminoimidazole carboxamide ribonucleotide transformylase (ATIC), inosine triphosphate pyrophosphatase (ITPA), methionine synthase (MTR) and methionine synthase reductase (MTRR).

DETAILED DESCRIPTION OF THE INVENTION

Figure 1:
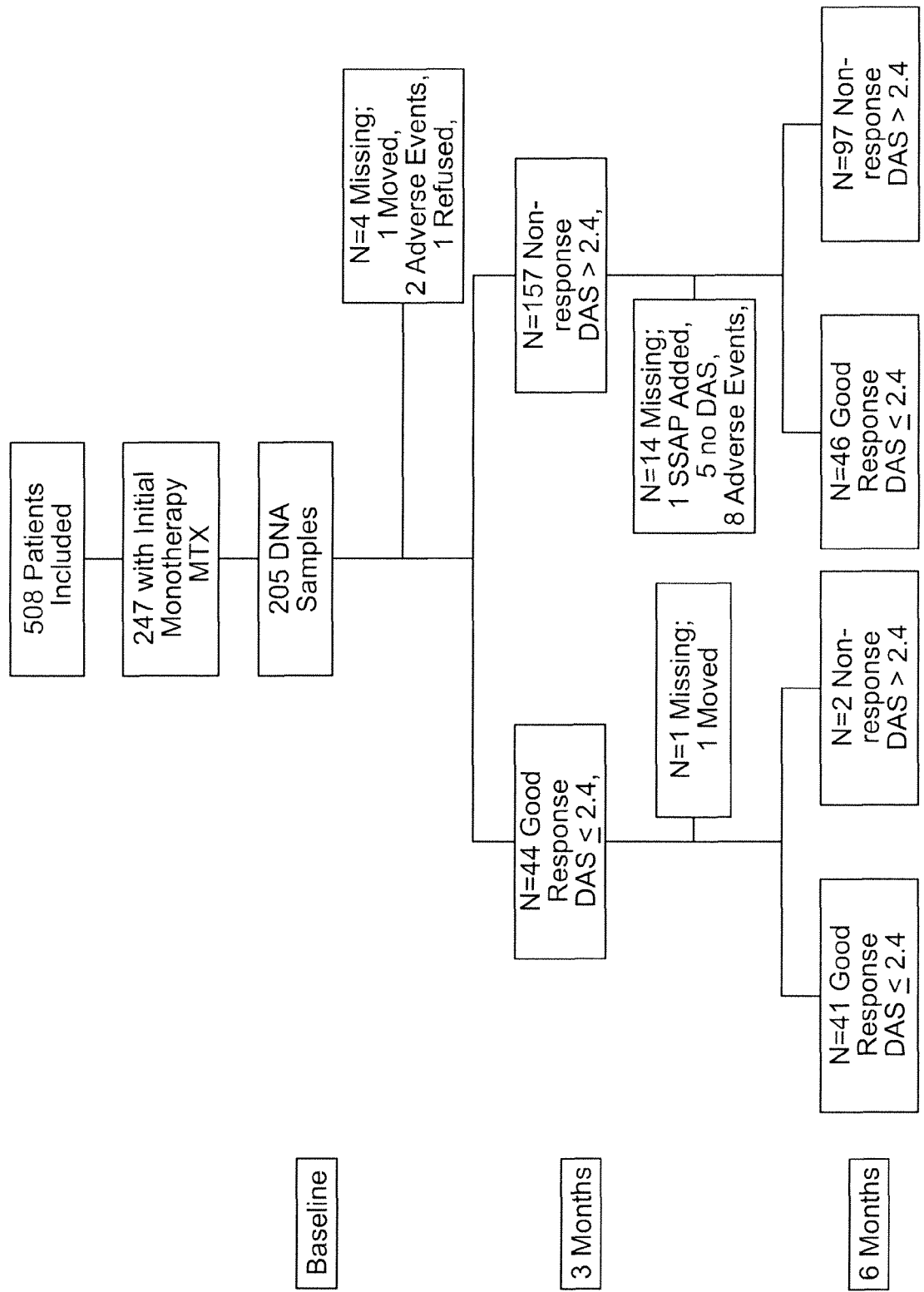
FIG. 1: Trial profile; SSAP=sulphasalazine; MTX=methotrexate; DAS=disease activity score.

The present invention exploits a newly established association of allelic variants in adenosine metabolism, also referred to as the adenosine release pathway, with clinical response in recent-onset RA patients treated with the antifolate methotrexate. Antifolates, or folate antagonists, are a group of compounds frequently used for cancer treatment. As used herein, the term "antifolate" means a molecule that is structurally similar to folate, and which acts as a folate antagonist against one or more folate-dependent enzymes (e.g., thymidylate synthase and dihydrofolate reductase). These compounds result in reduction de novo purine synthesis. One antifolate, methotrexate, is also used for treatment of rheumatoid arthritis.

Although the examples described herein relate to methotrexate, the present methods are also suitable for predicting efficacy and toxicity of other antifolates, including aminopterin, trimetrexate, lometrexol, pemetrexed, 5-fluorouracil and leucovorin, as well as methotrexate analogs. As used herein, the term "methotrexate analog" means a molecule having structural and functional similarity to methotrexate. Methotrexate analogs are functionally characterized, in part, by their inhibitory activity against dihydrofolate reductase. These analogs include, but are not limited to, dichloromethotrexate, 7-methyl substituted methotrexate, 3',5'-difluoromethotrexate, and 7,8-dihydro-8-methyl-methotrexate.

In one embodiment, the method of the invention determines polymorphisms, in particular single nucleotide polymorphisms (SNPs), in one or more adenosine pathway genes.

As used herein, "polymorphism" refers to the occurrence of two or more genetically determined alternative sequences or alleles in a population. A "polymorphic site" refers to the locus at which divergence occurs. Preferred polymorphic sites have at least two alleles, each occurring at frequency of greater than 1%, and more preferably greater than 10% or 20% of a selected population. A polymorphic locus may be as small as one base pair (single nucleotide polymorphism, or SNP). Polymorphic markers include restriction fragment length polymorphisms, variable number of tandem repeats (VNTR's), hypervariable regions, minisatellites, dinucleotide repeats, trinucleotide repeats, tetranucleotide repeats, simple sequence repeats, and insertion elements such as Alu. The first identified allele is arbitrarily designated as the reference allele and other alleles are designated as alternative or "variant alleles." The alleles occurring most frequently in a selected population is sometimes referred to as the "wild-type" allele. Diploid organisms may be homozygous or heterozygous for the variant alleles. The variant allele may or may not produce an observable physical or biochemical characteristic ("phenotype") in an individual carrying the variant allele. For example, a variant allele may alter the enzymatic activity of a protein encoded by a gene of interest.

A "single nucleotide polymorphism" or "SNP" occurs at a polymorphic site occupied by a single nucleotide, which is the site of variation between allelic sequences. The site is usually preceded by and followed by highly conserved sequences of the allele (e.g., sequences that vary in less than 1/100 or 1/1000 members of the populations). A SNP usually arises due to substitution of one nucleotide for another at the polymorphic site. A transition is the replacement of one purine by another purine or one pyrimidine by another pyrimidine. A transversion is the replacement of a purine by a pyrimidine or vice versa. Single nucleotide polymorphisms can also arise from a deletion of a nucleotide or an insertion of a nucleotide relative to a reference allele.

Adenosine pathway genes include, but are not limited to, adenosine monophosphate deaminase (AMPD1), aminoimidazole carboxamide ribonucleotide transformylase (ATIC), inosine triphosphate pyrophosphatase (ITPA), methionine synthase (MTR) and methionine synthase reductase (MTRR). In another embodiment, polymorphisms, particularly SNPs are determined in the AMPD1 and/or ITPA genes. In still another embodiment, polymorphisms, particularly SNPs, are detected in at least two of the adenosine pathway genes listed above. As described herein, the genetic profile of rheumatoid arthritis patients, in particular the profile for adenosine metabolism associated genes, is indeed a major determinant for response to methotrexate treatment.

Without wishing to be bound by any specific theory, adenosine is thought to mediate the antirheumatic effects of MTX via adenosine receptor signalling (39; 42; 43). Binding of this compound to specific receptors enhances the anti-inflammatory properties of methotrexate. For example, the AMPD1 34C>T mutation generates an AMP-deaminase enzyme with lower activity (40). AMPD1 catalyzes the conversion of adenosine-monophosphate (AMP) to inosine-monophosphate (IMP). Alternatively, AMP is converted to adenosine. Thus, deficiency of AMPD1 could enhance adenosine release. Other mutations and/or polymorphisms having an effect on AMPD1 activity in vivo may have similar or even more pronounced effects on MTX In addition, both ITPA and ATIC activity leads to formation of adenosine. ITPA polymorphisms have been shown to lead to ITPA deficiency (41), which results in decreased IMP levels as ITPA catalyzes the conversion of inosine triphosphate (ITP) to IMP. Since this enzyme influences the cellular IMP level, it influences its balance with AMP and adenosine. Furthermore, methotrexate inhibits ATIC which leads to cellular accumulation of AICAR, a nucleoside precursor (18; 24) which inhibits adenosine deaminase (ADA), resulting in reduced conversion of adenosine to inosine.

The present invention provides a method for determining responsiveness to methotrexate responsiveness in a mammal afflicted with, or at risk of developing rheumatoid arthritis (RA) by determining one or more polymorphisms (e.g. SNPs) in one or more genes in the adenosine pathway. The subject may be any mammal, including a human, ape, dog horse, cow, pig, rabbit and the like. In one embodiment, the method of the invention is performed in vitro on a sample obtained from a subject to be tested. The in vitro method is performed on nucleic acid present in the sample, such as a blood, serum, plasma, tissue, or buccal swab sample. Nucleic acids which can be analyzed using the present methods include genomic DNA, genomic RNA, mRNA and cDNA.

In one embodiment, polymorphisms in both alleles of 2, 3, 4, 5 or more genes involved in the adenosine release pathway are determined. In another embodiment, the gene to be analyzed for one or more polymorphisms (e.g., SNPs) is one or more of AMPD1, ATIC or IPTA. In addition, the detection of polymorphisms in the adenosine release pathway may be combined with polymorphisms in genes involved in other pathways such as the folate pathway which also plays a role in MTX responsiveness. Detection of other established RA diagnostic markers such as rheumatoid factor, C-reactive protein (CRP) and citrullinated antigens may be combined with detection of one or more polymorphisms in adenosine pathway genes.

In one embodiment, a SNP identifying an allelic variant selected from the group consisting of AMPD1 34C>T, ATIC 347 C>G, IPTA 94 A>C is identified. It will be appreciated that the present invention is not limited to these polymorphisms; other polymorphisms (e.g., SNPs) in any adenosine metabolism associated gene may be used, In another embodiment, the polymorphism has a frequency in a population of 1%, 5%, 10%, 20% or more, and results in an amino acid change resulting in a functional change for the gene product or enzyme. These functional changes include, but are not limited to, biochemical activity, stability/half-life and interaction with other proteins or compounds. Polymorphisms in non coding regions of a gene involved in the adenosine release pathway, leading to altered rates of transcription and regulation or splicing, may also be used. Silent polymorphisms in coding regions, which have no effect on the translated protein, may affect translation rates or efficiency and thereby affect the adenosine release pathway. These polymorphisms may also be used in the diagnostic methods described herein.

The present methods may be performed using any known biological or biochemical method in which genetic polymorphisms, such as SNPs, can be detected or visualized. Such methods include, but are not limited to, DNA sequencing, allele specific PCR, PCR amplification followed by an allele/mutant specific restriction digestion, oligonucleotide ligation assays, primer hybridization and primer extension assays, optionally combined with or facilitated by microarray analysis. Alternative methods for determining allelic variants and gene polymorphisms are readily available to the skilled person in the art of molecular diagnostics.

The invention also provides oligonucleotides capable of hybridizing to sequences in or flanking genes (e.g., polymorphic regions) involved in adenosine metabolism, and the use of these oligonucleotides for performing these methods. Primers may be designed to amplify (e.g., by PCR) at least a fragment of a gene encoding an adenosine metabolism associated enzyme. A polymorphism may be present within the amplified sequence and may be detected by, for example, a restriction enzyme digestion or hybridization assay. The polymorphism may also be located at the 3' end of the primer or oligonucleotide, thus providing means for an allele or polymorphism specific amplification, primer extension or oligonucleotide ligation reaction, optionally with a labeled nucleotide or oligonucleotide. The label may be an enzyme (e.g., alkaline phosphatase, horseradish peroxidase), radiolabel ($^{32}P$, $^{33}P$, $^{3}H$, $^{125}I$, $^{35}S$ etc.), a fluorescent label (Cy3, Cy5, GFP, EGFP, FITC, TRITC and the like) or a hapten/ligand (e.g., digoxigenin, biotin, HA, etc.). In one embodiment, the detection is carried out using oligonucleotides physically linked to a solid support, and may be performed in a microarray format.

The present invention also includes a kit of parts comprising one or more, oligonucleotides capable of hybridizing to, or adjacent to, polymorphic sites in a gene, or two or more genes, involved in adenosine metabolism as described above. The oligonucleotide(s) may be provided in solid form, in solution or attached on a solid carrier such as a DNA microarray. In addition, the kit may provide detection means, containers comprising solutions and/or enzymes and a manual with instructions for use.

EXAMPLES

Methods

Patients

The 247 patients enrolled in the study was a sub-cohort of 508 patients participating in the BeSt trial (25). Inclusion criteria for this trial were fulfillment of the American College of Rheumatology (ACR) 1987 criteria, age of 18 years or older, a disease duration of less than 2 years. All patients had to have an active disease defined as $\geq$6/66 swollen joints and $\geq$6/68 tender joints and either an ESR $\geq$28 mm/hr or a Visual Analogue Scale (VAS) for global health $\leq$20 mm (on a scale of 0-100, 0=worst, 100=best).

Individuals were ineligible if they previously were treated with DMARDs other than antimalarials. Other exclusion criteria included: concomitant treatment with an experimental drug; a malignancy within the last 5 years; bone marrow hypoplasia, a serum ASAT/ALAT>3 times the upper limit of normal; a serum creatinine >150 µmol/l or an estimated creatinine clearance of <75 ml/min; diabetes mellitus; alcohol or drug abuse; pregnancy or the wish to become pregnant during the study period or inadequate contraception. The local ethics committee in each participating hospital approved the study and all patients signed informed consent before inclusion.

Study Design

The BeSt trial is a randomized, multi-centre, single-blinded, clinical study comparing the clinical efficacy of four different treatment strategies in early rheumatoid arthritis; sequential monotherapy (n=126 starting with methotrexate), step-up to combination therapy with sulphasalazine (n=121 starting with methotrexate), initial combination therapy with methotrexate, sulphasalazine and a high tapered dose of prednisolone (n=133) or initial biologic therapy with infliximab and methotrexate (n=128). In the present study, only patients allocated to initial single use of methotrexate were selected (n=247).

The primary objective of treatment in the BeSt study was achieving good clinical response as defined by the DAS$\leq$2.4 (26-28). The DAS is a validated composite outcome measure consisting of the Ritchie articular index (RAI), the number of swollen joints (SJC, out of 44), general well being as indicated by the patient on a visual analogue scale (VAS), and the Erythrocyte Sedimentation Rate (ESR). A research nurse who remained blinded for the allocated treatment group scored the DAS every three months.

All selected patients started with oral methotrexate 7.5 mg weekly, increased to 15 mg weekly after 4 weeks, combined with folic acid (1 mg per day). In case of insufficient clinical response at three months of follow-up (DAS>2.4), the dosage was increased stepwise to 25 mg weekly, either orally or parenterally as decided by the rheumatologist. If the clinical response remained insufficient with methotrexate 25 mg weekly, patients were treated according to the next step of the BeSt protocol; patients with methotrexate sequential monotherapy switched to sulphasalazine 1000 mg twice daily; patients with initial step-up combination therapy, sulphasalazine 1000 mg twice daily was added to methotrexate. Concomitant therapies with nonsteroidal anti-inflammatory drugs (NSAIDs), as well as intra-articular injections with corticosteroids, were allowed for all treatment groups. For current analysis, clinical data for the first six months of follow-up were used, representing methotrexate treatment only.

"Responders" were defined as patients with DAS≦2.4 (good clinical response) based on EULAR response criteria (26-28) and 'non-responders' as patients with DAS>2.4 at six months of follow up.

Toxicity was evaluated by counting each reported adverse drug event and its consequences for the patient and treatment. Adverse drug events were spontaneously reported by the patients, or were reported as a result of non-specific questioning on patients' well-being by the investigator, by physical examination or laboratory measurements during follow up. In case of adverse drug events, methotrexate was continued at the lowest tolerated dose, or if methotrexate was not tolerated at all, the DMARD therapy was adjusted according to the protocol. Of all reported adverse drug events, the following non-infectious adverse drug events were evaluated explicitly: gastrointestinal adverse drug events defined as patients' general well-being, nausea, vomiting, diarrhea, and constipation; liver adverse drug events defined as all cases of elevated functional liver enzymes resulting in methotrexate dose adjustment or discontinuation; pneumonitis; skin and mucosal disorders. Moreover, patients were evaluated for leucopenia (<4.10$^9$/L), ALAT 3 times upper limit of normal (>135 U/L) and for alkaline phosphatase (AF) 3 times the upper limit of normal (>360 U/L).

Five single nucleotide polymorphisms (SNPs) in genes related to adenosine release were selected using the following criteria; validated SNP; SNP causes non-synonymous amino acid change; indications for clinical relevance from previous publications (15; 20-24); a preferred minimal genotype frequency of approximately 10%. The five selected genes encode adenosine monophosphate deaminase (AMPD1), aminoimidazole carboxamide ribonucleotide transformylase (ATIC), inosine triphosphate pyrophosphatase (ITPA), methionine synthase (MTR), methionine synthase reductase (MTRR). The following SNPs were analysed: MTRR 66A>G (rs1801394), MTR 2756A>G (rs1805087), AMPD1 34C>T (rs17602729), ITPA94 C>A (rs1127354), ATIC 347C>G (rs2372536).

DNA was isolated from peripheral white blood cells by standard manual salting out method. Positive controls (Applied Biosystems Control DNA CEPH 347-02) and negative controls (water) were used. In addition, 5-10% of samples were genotyped in duplicate and no inconsistencies were observed.

Genotyping was performed using real-time PCR with Taqman® according to protocols provided by the manufacturer (Taqman, Applied Biosystems, Foster City, Calif., USA). Genotype frequencies showed Hardy-Weinberg equilibrium and the success rate was 99.5% for MTRR 66A>G; 100% for MTR 2756A>G; 99.5% for AMPD1 34C>T; 99.5% for ITPA 94AC; 100% for ATIC 347C>G. Genotype distributions were for AMPD1 34C>T 74% CC; 25% CT; 1% TT, for MTRR 66A>G 20% AA; 53% AG; 28% GG, for MTR 2756A>G 70% AA; 27% AG; 2% GG, for ITPA94 C>A 85% CC; 15% CA; 0% AA and for ATIC 347C>G 47% CC; 45% CG; 8% GG, respectively.

Statistical Analysis

Differences in baseline characteristics were analysed by Student's t-test for continuous variables or Chi-square test for dichotomous variables. Differences in genotype distribution for response and toxicity were tested by 3 by 2 cross tabs for each genotype, and by 2 by 2 cross tabs for carriers versus non-carriers analysis with the two-sided Chi-square test. We used binary logistic analysis in case of differences in genotype distribution, to calculate odds ratios for achieving good response or experiencing adverse drug events. Age and gender were identified as possible confounders and were used as covariates in all regression analyses. The primary efficacy endpoint was good clinical response at six months (DAS≦2.4). DAS good clinical response status required patients to be present at a given time point; no values were carried forward. Secondary endpoints were good clinical improvement defined as change in DAS>1.2 (ΔDAS>1.2) and moderate clinical improvement defined as change in DAS>0.6 (ΔDAS>0.6). Additionally, for efficacy analyses, the following possible confounders were identified: DAS at baseline, duration of joint complaints before inclusion, time between RA diagnosis and inclusion, presence of rheumatoid factor (Rf+), Sharp van der Heijde score at baseline, ESR, RAI and C-reactive protein (CRP).

For toxicity analysis, all patients who altered therapy from methotrexate before six months of follow-up were verified for adverse drug events after change of therapy and included in the analysis. The analyses of laboratory measurements were performed for completers only. The toxicity regression analysis was tested for the following confounders: weight, creatinine clearance, methotrexate dosage group (15 or 25 mg) and use of alcohol.

All statistical analyses were performed using SPSS 11.5 software (SPSS inc, Chicago Ill., USA). Five hypotheses were tested; MTRR 66A>G, MTR 2756A>G AMPD1 34C>T, ITPA94 C>A, ATIC 347C>G are associated with methotrexate treatment outcome. Therefore, Bonferroni adjustment was performed for multiple comparisons. Both adjusted and unadjusted values P-values were presented. P-values <0.05 were considered significant.

Example 1

Of the 247 patients randomized to methotrexate monotherapy in BeSt, 205 DNA samples were obtained. There were no statistically significant differences in baseline characteristics between patients with and without DNA samples. Clinical and demographic data of the genotyped rheumatoid arthritis population are presented in table 1. The reported ethnicity in our population was 93% Caucasian (n=191), 2.4% Asian (n=5), 1.0% African (n=2), 3.4% other (n=3 Hindustan, n=3 Surinam, n=1 Israeli). Performing the analyses without non-Caucasian patients did not alter the results.

| Characteristics | Baseline value |
|---|---|
| Demographic | |
| Gender [female/male %] | 68.8/31.2 |
| Age [years] (sd) | 54.6 (±13.3) |
| RF positivity [%] | 67.3 |
| Disease duration in weeks [median] (range) | 2.0 (0-104.7) |
| Measures of disease activity | |
| Duration of joint complaints in weeks [median] (range) | 25.0 (1.1-584.3) |
| DAS(sd) | 4.5 (±0.8) |
| ESR [median mm/hr] (range) | 38 (2-143) |

| Characteristics | Baseline value |
| --- | --- |
| CRP [median mg/L] (range) | 23 (0-238) |
| RAI [median] (range) | 13 (2-47) |
| Swollen joints [median] (range) | 13 (3-36) |
| Sharp van der Heijde score [median] (range) | 4 (4-49.5) |

At six months, the percentage responders (DAS≦2.4) was 47% (n=87); of them 48% were using 15 mg methotrexate weekly and 52% were using 25 mg methotrexate weekly (FIG. 1).

Figure 2:
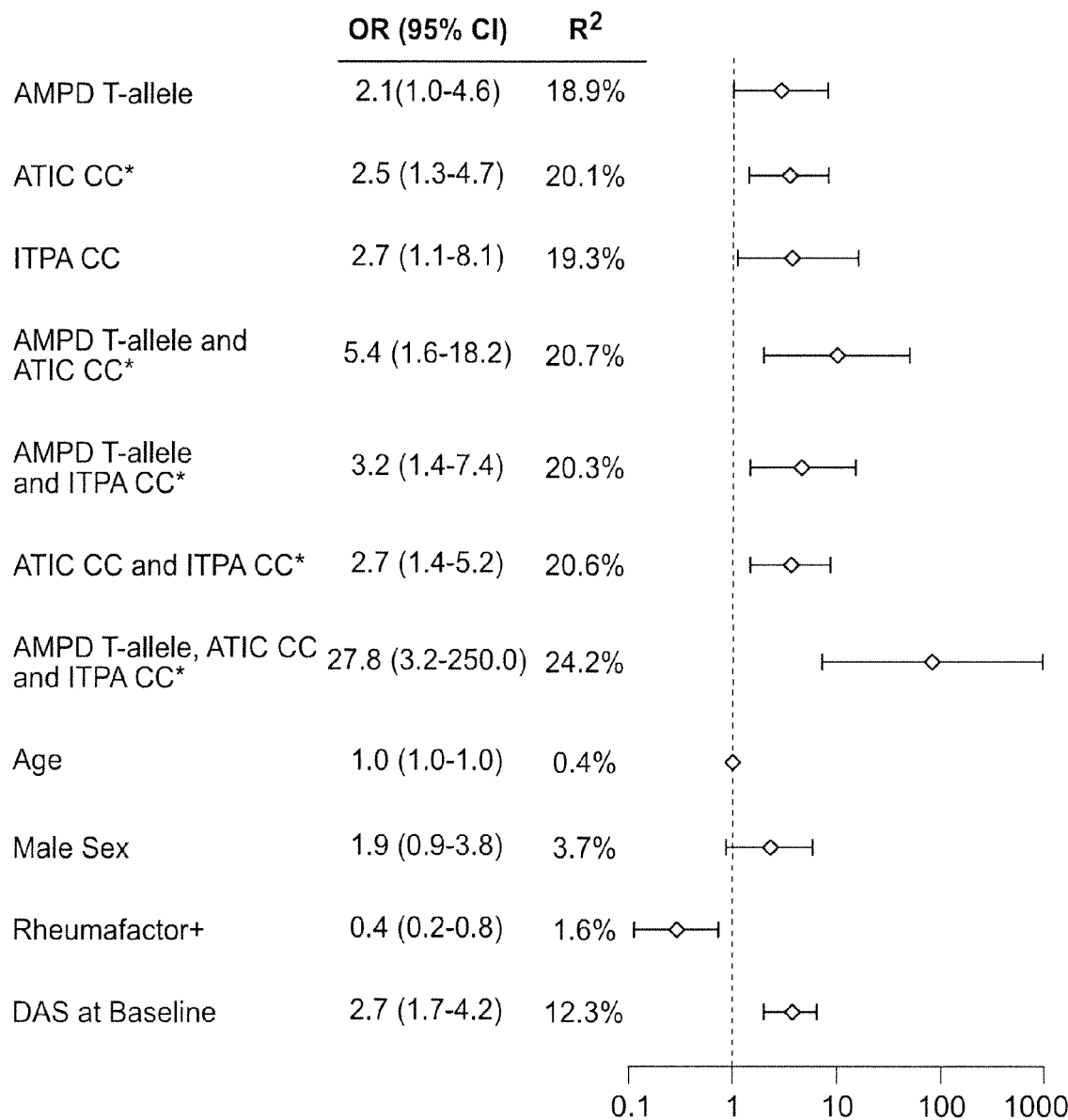
FIG. 2: Associations of AMPD1 34C>T, ATIC 347C>G and ITPA 94A>G polymorphisms with good clinical response with methotrexate therapy. Data presented are odds ratios resulting from carrier analysis e.g. CC vs. CT and TT genotyped (95% confidence intervals), with correction for confounders age, gender, presence of rheumatoid factor and DAS at baseline. Odds ratios presented for age, gender, presence of rheumatoid factor and DAS at baseline are results found without genotypes as independent variables. *p<0.05 if Bonferroni adjusted. Explained variances for genotype or combination genotypes are shown with confounders included.

Three out of the five selected genetic polymorphisms were associated with good clinical response at six months of follow up (FIG. 2). Patients carrying the AMPD1 T-allele were 2.1 times more likely to achieve good clinical response when compared to patients with the AMPD1 CC variant. For ATIC and ITPA an association was found for patients with the CC genotype and good clinical response (FIG. 2). The number and percentages of responders per genotype are presented in table 2.

TABLE 2

Number of patients (percentage) per AMPD1, ATIC and ITPA genotypes; comparisons for methotrexate response and overall adverse drug events

|  | AMPD1** | | | ATIC | | | ITPA** | |
| --- | --- | --- | --- | --- | --- | --- | --- | --- |
|  | CC | CT | TT | CC | CG | GG | CC | CA |
| Population | 151 (73%) | 50 (24%) | 3 (2%) | 97 (47%) | 92 (45%) | 16 (8%) | 174 (85%) | 30 (15%) |
| Good clinical response at six months | 57 (38%) | 28 (56%) | 1 (33%) | 51 (53%) | 30 (33%) | 6 (38%) | 79 (45%) | 7 (23%) |
| Methotrexate 15 mg weekly | 25/36 (69%) | 15/15 (100%) | 1/1 (100%) | 22/25 (88%) | 15/22 (68%) | 4/5 (80%) | 38/47 (81%) | 3/5 (60%) |
| Methotrexate 25 mg weekly | 30/98 (31%) | 13/29 (45%) | 0/2 (0%) | 28/61 (46%) | 14/60 (23%) | 2/9 (22%) | 39/107 (36%) | 4/22 (18%) |
| Adverse drug events at six months | 42/146 (29%) | 16/50 (32%) | 1/3 (33%) | 21/94 (22%) | 33/91 (36%) | 6/15 (40%) | 51/169 (30%) | 8/30 (27%) |

AMPD1 = adenosine monophosphate deaminase, ATIC = aminoimidazole carboxamide ribonucleotide transformylase, ITPA = inosine triphosphate pyrophosphatase. MTRR and MTR were not associated with methotrexate efficacy and toxicity.
**One patient missing (0.5% of total population).

Example 2

To assess if these three favourable polymorphisms showed an additive effect on methotrexate response, additional analysis was performed for each combination of the genotypes AMPD1, ATIC and ITPA. For patients carrying the combinations AMPD1 T-allele and ATIC CC (n=22), AMPD1 T-allele and ITPA CC (n=41), and ATIC CC and ITPA CC (n=82), the percentages of good clinical response at six months was 68, 63 and 56 respectively. In patients carrying all the favourable genotypes (n=16), a further increase in response rate was seen (88%). Logistic regression analyses showed an odds ratio for achieving good clinical response of 27.8 for this group. The explained variance ($R^2$) of these combined favourable genotypes to methotrexate treatment response was 24% (FIG. 2). In contrast, if patients carried all three unfavourable genotypes (n=10), which were the AMPD CC and the ITPA CA genotype and the ATIC G-allele, the response rate at six months was only 10%.

After adjustment for multiple comparisons, the association of the ATIC CC genotyped with methotrexate response remained significant (p=0.007). In addition, the combinations of favourable AMPD1, ATIC and ITPA genotypes remained significantly associated to good clinical response (FIG. 2). The regression analysis with good clinical improvement also revealed an association for ATIC CC genotype in comparison with G-allelic carriers (OR2.5; 95% CI 1.3-4.8, p=0.007). Data showed no associations for the MTRR and MTR polymorphisms with good clinical response.

In the regression analysis to predict good clinical response, only DAS at baseline and a positive test for Rheumatoid Factor (RF+) appeared to be significant clinical predictors for good clinical response (FIG. 2). We investigated if these clinical characteristics were affected by genotype. No significant associations of clinical predictors with genotype variants were observed.

The number of patients of whom toxicity data were available at six months was 200 since 4 patients did not show up at six months of follow-up and 1 patient moved. Thirty percent (n=60) of the study population experienced at least one adverse drug event during six months of treatment (table 3). The percentage of patients experiencing an adverse drug event was similar for both dose groups, although patients with 25 mg methotrexate weekly discontinued therapy more frequently than patients with 15 mg weekly due to adverse drug events (FIG. 1).

Figure 3:
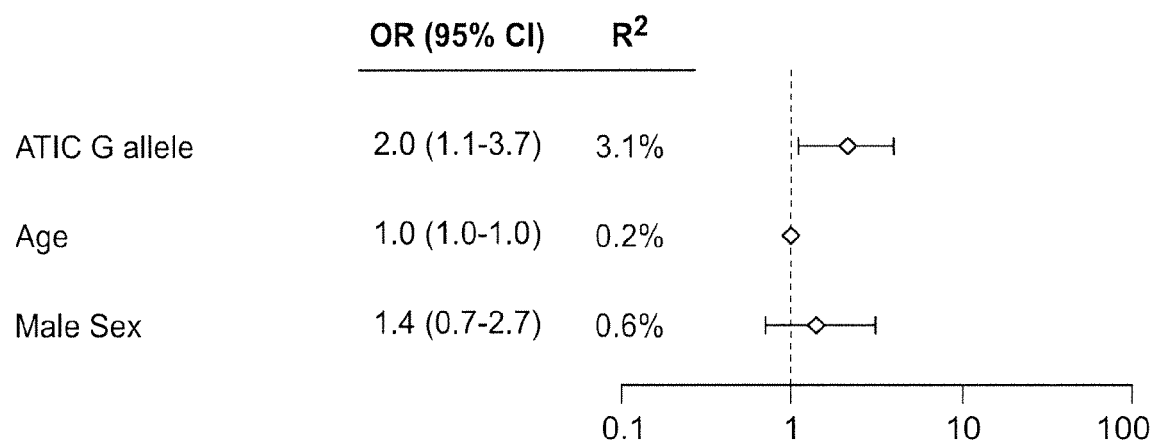
FIG. 3: Association of ATIC 347C>G polymorphism with the occurrence of adverse drug events during 6 months of methotrexate therapy. Data presented are odds ratios resulting from carrier analysis e.g. CC vs. CG and GG genotyped (95% confidence intervals), with correction for confounders age, gender.

During six months of treatment, patients carrying ATIC G-allele were 2 times more likely to experience any adverse drug event (FIG. 3). After adjustment for multiple comparisons, the association for the ATIC G-allele and adverse drug events did not remain significant. Data showed no other associations with methotrexate induced adverse events. In the logistic regression analysis, none of the clinical characteristics was predictive for experiencing adverse drug events.

We examined the interaction of good clinical response (DAS≦2.4) at six months, the genotypes for AMPD1, ATIC and ITPA and the occurrence of adverse drug events. In order to ascertain if patients with favourable genotypes were not predisposed to more toxicity, responders at six months were selected (n=99) and regression analyses were carried out. In general, patients with good clinical response at six months experienced less adverse drug events when compared to non-responders (OR 0.45; 95% CI 0.22, 0.91). This finding was also confirmed by the observation that non-responders carrying the ATIC G-allele had an increased risk for adverse drug events (OR 2.8, 95% CI 1.1, 7.5) as compared to all ATIC G-allele carriers.

For responders carrying the AMPD1 T-allele or the ATIC CC genotype or the ITPA CC genotype or combinations of these genotypes, no associations were found with the occurrence of adverse drug events. The numbers and percentages of patients experiencing adverse drug events per genotype for AMPD1, ATIC and ITPA are presented in table 2.

TABLE 3

Number of patients (percentage) with adverse drug events during six months of treatment.

| Adverse Drug Event | Frequency at 6 months |
|---|---|
| Skin and mucosa disorders | 17 (8.5%) |
| Pneumonitis | 0 (0%) |
| Hepatic elevated liver enzymes | 16 (8%) |
| Gastrointestinal (general wellbeing, nausea, vomiting, diarrhoea, constipation) | 26 (13.0%) |
| Total population (Overall adverse drug events) | 60 (30%) |

This invention exploits a newly established association of allelic variants in adenosine pathway, in particular adenosine monophosphate deaminase (AMPD1), aminoimidazole carboxamide ribonucleotide transformylase (ATIC) and inosine triphosphate pyrophosphatase (ITPA) genes, with clinical response in recent-onset RA patients treated with methotrexate. Patients carrying the favourable AMPD1 T-allele, the ATIC CC genotype or the ITPA CC genotype were 2 to 3 times more likely to show good clinical response following six months of methotrexate therapy. Additionally, the good clinical response rate was increased substantially for patients carrying three favourable genotypes.

For the occurrence of adverse drug events, only an association was found for the ATIC G-allelic carriers. This association was not significant when adjusted for multiple testing. No associations for methionine synthase (MTR) and methionine synthase reductase (MTRR) were found with methotrexate efficacy or toxicity.

The study was chosen to assess genetic markers for treatment outcome because it provided clear and objectified outcome measures with standardized treatment regimens in a well-described rheumatoid arthritis population. The methotrexate dosages used mimic current clinical practice and evaluation of DMARDs therapy has been shown to be appropriate at six months treatment (29).

The primary efficacy endpoint was set at good clinical response at six months of methotrexate treatment, whereas remission has been described as primary goal in other reports (7; 29; 30). To examine if the identified genotypes for good clinical response at six months, were also predictive for remission at one year of follow up, an additional analyses for good clinical responders carrying the ATIC CC genotype was done. Remission defined as DAS<1.6 was determined for this variant at one-year of follow-up. Data showed that 35% of all patients (n=97) carrying the ATIC CC genotype were in remission, whereas other research showed 10-25% of the patients in remission (8; 31). This observation indicated that this variant is indicative for prolonged and increased response.

The adjustment of our results for multiple testing minimizes false positive associations, but it also increased the chance of making type II errors due to the conservative nature of the Bonferroni adjustment (32; 33). Therefore, both adjusted and unadjusted values were presented.

The data showed that methotrexate therapy was less beneficial for ATIC G-allelic carriers, ITPA A-allelic carriers and AMPD1 CC genotyped patients. In fact, 47% of the overall population showed good clinical response at 6 months. Yet, if good clinical response was compared for allelic variants, the response percentages were 58% for ATIC CC patients and 37% for the G-allelic carriers. For ITPA CC genotyped, the response percentage was 50% when compared to 26% for the A-allelic carriers and for AMPD1 T-allelic carriers, the response was 60% when compared to 42% for the AMPD1 CC genotyped patients. Therefore, the results indicate that pharmacogenetic testing before starting therapy may help to guide clinical treatment decisions for example in selecting the patients with all three favourable genotypes, with a high chance of efficacy upon MTX treatment. As another example for such clinical use, the patients were analyzed with all three unfavourable genotypes, which were the ATIC G-allele and the AMPD1 CC and the ITPA CC genotype. In these patients other DMARD therapy than MTX may be chosen as their response rate at 6 months was only 10%. Thus, this pharmacogenetic test could avoid ineffective treatment and at the same time indicate effective therapy in 13% of the rheumatoid arthritis population.

The polymorphisms in the genes tested were selected on the basis of candidate gene approach (15; 20-24; 34). Although the effect of the variant alleles in relation to adenosine homeostasis has not yet been explored, several in vitro effects have been shown (36-41). In summary, in this example patients were identified, using the diagnostic method of the invention, having adenosine genotypes who were most likely to achieve good clinical response with methotrexate. The pharmacogenetic strategy provided markers in the adenosine pathway, in particular A TIC, ITPA en AMPD1 genes allelic variants, which will help to guide clinical treatment decisions for patients with early rheumatoid arthritis to suppress disease activity adequately.

REFERENCE LIST

1. Anderson J J, Wells G, Verhoeven A C, Felson D T. Factors predicting response to treatment in rheumatoid arthritis: the importance of disease duration. Arthritis Rheum 2000; 43(1):22-9.
2. Pincus T. Long-term outcomes in rheumatoid arthritis. Br. J. Rheumatol. 1995; 34 Suppl 2:59-73.
3. Aletaha D, Smolen J S. The rheumatoid arthritis patient in the clinic: comparing more than 1,300 consecutive DMARD courses. Rheumatology (Oxford) 2002; 41(12): 1367-74.
4. Smolen J S, Aletaha D, Machold K P. Therapeutic strategies in early rheumatoid arthritis. Best. Pract. Res. Clin. Rheumatol. 2005; 19(1):163-77.
5. O'Dell J R, Haire C E, Erikson N, Drymalski W, Palmer W, Eckhoff P J et al. Treatment of rheumatoid arthritis with methotrexate alone, sulfasalazine and hydroxychloroquine, or a combination of all three medications. N Engl J Med 1996; 334(20):1287-91.
6. Pincus T, Yazici Y, Sokka T, Aletaha D, Smolen J S. Methotrexate as the "anchor drug" for the treatment of early rheumatoid arthritis. Clin. Exp. Rheumatol. 2003; 21(5 Suppl 31):S179-S185.
7. Klareskog L, van der Heijde D, de Jager J P, Gough A, Kalden J, Malaise M et al. Therapeutic effect of the combination of etanercept and methotrexate compared with each treatment alone in patients with rheumatoid arthritis: double-blind randomised controlled trial. The Lancet 2004; 363(9410):675-81.
8. Mottonen T, Hannonen P, Leirisalo-Repo M, Nissila M, Kautiainen H, Korpela M et al. Comparison of combination therapy with single-drug therapy in early rheumatoid arthritis: a randomised trial. FIN-RACo trial group. Lancet 1999; 353(9164):1568-73.
9. Genovese M C, Bathon J M, Martin R W, Fleischmann R M, Tesser J R, Schiff M H et al. Etanercept versus methotrexate in patients with early rheumatoid arthritis: two-year radiographic and clinical outcomes. Arthritis Rheum 2002; 46(6):1443-50.
10. Matteson E L, Weyand C M, Fulbright J W, Christianson T J H, McClelland R L, Goronzy J J. How aggressive should initial therapy for rheumatoid arthritis be? Factors associated with response to 'non-aggressive' DMARD treatment and perspective from a 2-yr open label trial. Rheumatology 2004; 43(5):619-25.
11. Verstappen S M, Jacobs J W, Bijlsma J W, Heurkens A H, Booma-Frankfort C, Borg E J et al. Five-year followup of rheumatoid arthritis patients after early treatment with disease-modifying antirheumatic drugs versus treatment according to the pyramid approach in the first year. Arthritis Rheum 2003; 48(7):1797-807.
12. Evans W E, McLeod H L. Pharmacogenomics—drug disposition, drug targets, and side effects. N. Engl. J. Med. 2003; 348(6):538-49.
13. Rocha J C, Cheng C, Liu W, Kishi S, Das S, Cook E H et al. Pharmacogenetics of outcome in children with acute lymphoblastic leukemia. Blood 2005; 105(12):4752-8.
14. Israel E, Chinchilli V M, Ford J G, Boushey H A, Cherniack R, Craig T J et al. Use of regularly scheduled albuterol treatment in asthma: genotype-stratified, randomised, placebo-controlled cross-over trial. Lancet 2004; 364(9444):1505-12.
15. Dervieux T, Furst D, Lein D O, Capps R, Smith K, Walsh M et al. Polyglutamation of methotrexate with common polymorphisms in reduced folate carrier, aminoimidazole carboxamide ribonucleotide transformylase, and thymidylate synthase are associated with methotrexate effects in rheumatoid arthritis. Arthritis Rheum 2004; 50(9):2766-74.
16. Urano W, Taniguchi A, Yamanaka H, Tanaka E, Nakajima H, Matsuda Y et al. Polymorphisms in the methylenetetrahydrofolate reductase gene were associated with both the efficacy and the toxicity of methotrexate used for the treatment of rheumatoid arthritis, as evidenced by single locus and haplotype analyses. Pharmacogenetics 2002; 12(3):183-90.
17. Wessels J. A. M., Vries-Bouwstra, J., Heijmans, B. T., Slagboom, P. E., Goekoop-Ruiterman, Y. P., Allaart, C. F., Kerstens, P. J., Zeben, D., Breedveld, F. C., Dijkmans, B. A., Huizing a, T. W., and Guchelaar, H. J. Efficacy and toxicity of methotrexate nearly rheumatoid arthritis is associated with single nucleotide polymorphisms in genes coding for folate pathway enzymes. Arthritis and Rheumatism. 2005. In Press
18. Cronstein B N. Low-dose methotrexate: a mainstay in the treatment of rheumatoid arthritis. Pharmacol. Rev. 2005; 57(2):163-72.
19. Nakamachi Y, Koshiba M, Nakazawa T, Hatachi S, Saura R, Kurosaka M et al. Specific increase in enzymatic activity of adenosine deaminase 1 in rheumatoid synovial fibroblasts. Arthritis Rheum 2003; 48(3):668-74.
20. Kalsi K K, Yuen A H, Rybakowska I M, Johnson P H, Slominska E, Birks E J et al. Decreased cardiac activity of AMP deaminase in subjects with the AMPD I mutation—a potential mechanism of protection in heart failure. Cardiovasc. Res. 2003; 59(3):678-84.
21. Marinaki A M, Ansari A, Duley J A, Arenas M, Sumi S, Lewis C M et al. Adverse drug reactions to azathioprine therapy are associated with polymorphism in the gene encoding inosine triphosphate pyrophosphatase (ITPase). Pharmacogenetics 2004; 14(3):181-7.
22. Bosco P, Gueant-Rodriguez R M, Anello G, Barone C, Namour F, Caraci F et al. Methionine synthase (MTR) 2756 (A→G) polymorphism, double heterozygosity methionine synthase 2756 AG/methionine synthase reductase (MTRR) 66 AG, and elevated homocysteinemia are three risk factors for having a child with Down syndrome. Am. J Med. Genet. A 2003; 121(3):219-24.
23. Gaughan D J, Kluijtmans L A, Barbaux S, McMaster D, Young I S, Yarnell J W et al. The methionine synthase reductase (MTRR) A66G polymorphism is a novel genetic determinant of plasma homocysteine concentrations. Atherosclerosis 2001; 157(2):451-6.
24. Bulock K G, Beardsley G P, Anderson K S. The kinetic mechanism of the human bifunctional enzyme ATIC (5-amino-4-imidazolecarboxamide ribonucleotide transformylase/inosine 5'-monophosphate cyclohydrolase). A surprising lack of substrate channeling. J. Biol. Chem. 2002; 277(25):22168-74.
25. Goekoop-Ruiterman Y P, Vries-Bouwstra J K, Allaart C F, van Zeben D, Kerstens P J, Hazes J M et al. Clinical and radiographic outcomes of four different treatment strategies in patients with early rheumatoid arthritis (the BeSt study): a randomized, controlled trial Arthritis Rheum 2005; 52(11):3381-90.
26. van Gestel A M, Prevoo M L, 't H of M A, van Rijswijk M H, van de Putte L B, van Riel P L. Development and validation of the European League Against Rheumatism response criteria for rheumatoid arthritis. Comparison with the preliminary American College of Rheumatology and the World Health Organization/International League Against Rheumatism Criteria. Arthritis Rheum 1996; 39(1):34-40.
27. van der Heijde D M, van 't H M, van Riel P L, van de Putte L B. Development of a disease activity score based on judgment in clinical practice by rheumatologists. J. Rheumatol. 1993; 20(3):579-81.
28. Aletaha D, Ward M M, Machold K P, Nell V P, Stamm T, Smolen J S. Remission and active disease in rheumatoid arthritis: defining criteria for disease activity states. Arthritis Rheum 2005; 52(9):2625-36.
29. Puolakka K, Kautiainen H, Mottonen T, Hannonen P, Korpela M, Hakala M et al. Early suppression of disease activity is essential for maintenance of work capacity in patients with recent-onset rheumatoid arthritis: five-year experience from the FIN-RACo trial. Arthritis Rheum 2005; 52(1):3641.
30. Verstappen S M M, Albada-Kuipers G A, Bijlsma J W J, Blaauw A A M, Schenk Y, Haanen H C M et al. A good response to early DMARD treatment of patients with rheumatoid arthritis in the first year predicts remission during follow up. Ann Rheum Dis 2005; 64(1):3843.
31. Gossec L, Dougados M, Goupille P, Cantagrel A, Sibilia J, Meyer O et al. Prognostic factors for remission in early rheumatoid arthritis: a multiparameter prospective study. Ann Rheum Dis 2004; 63(6):675-80.
32. Huizing a T W, Pisetsky D S, Kimberly R P. Associations, populations, and the truth: recommendations for genetic association studies in Arthritis & Rheumatism. Arthritis Rheum 2004; 50(7):2066-71.
33. Newton-Cheh C, Hirschhorn J N. Genetic association studies of complex traits: design and analysis issues. Mutat. Res. 2005; 573(1-2):54-69.
34. Hattersley A T, McCarthy M I. What makes a good genetic association study? Lancet 2005; 366(9493):1315-23.
35. Ioannidis J P, Ntzani E E, Trikalinos T A, Contopoulos-Ioannidis D G. Replication validity of genetic association studies. Nat. Genet. 2001; 29(3):306-9.
36. Morabito L, Montesinos M C, Schreibman D M, Balter L, Thompson L F, Resta R et al. Methotrexate and sulfasalazine promote adenosine release by a mechanism that requires ecto-5'-nucleotidase-mediated conversion of adenine nucleotides. J. Clin. Invest 1998; 101 (2):295-300.

37. Cronstein B N, Eberle M A, Gruber H E, Levin R I. Methotrexate inhibits neutrophil function by stimulating adenosine release from connective tissue cells. Proc. Natl. Acad. Sci. U.S.A. 1991; 88(6):2441-5.

38. Delano D L, Montesinos M C, Desai A, Wilder T, Fernandez P, D'Eustachio P et al. Genetically based resistance to the antiinflammatory effects of methotrexate in the air-pouch model of acute inflammation. Arthritis Rheum 2005; 52(8):2567-75.

39. Montesinos M C, Desai A, Delano D, Chen J F, Fink J S, Jacobson M A et al. Adenosine A2A or A3 receptors are required for inhibition of inflammation by methotrexate and its analog MX-68. Arthritis Rheum 2003; 48(1):240-7.

40. Morisaki T, Gross M, Morisaki H, Pongratz D, Zollner N, Holmes E W. Molecular basis of AMP deaminase deficiency in skeletal muscle. Proc. Natl. Acad. Sci. U.S.A. 1992; 89(14):6457-61.

41. Cao H, Hegele R A. DNA polymorphisms in ITPA including basis of inosine triphosphatase deficiency. J. Hum. Genet. 2002; 47(11):620-2.

42. Cutolo M, Sulli A, Pizzorni C, Seriolo B, Straub R H. Anti-inflammatory mechanisms of methotrexate in rheumatoid arthritis. Ann Rheum Dis 2001; 60(8):729-35.

43. Chan E S, Cronstein B N. Molecular action of methotrexate in inflammatory diseases. Arthritis Res. 2002; 4(4): 266-73.

What is claimed:

1. A method for determining clinical responsiveness to methotrexate therapy in a human subject afflicted with, or at risk of developing, rheumatoid arthritis comprising detecting in a nucleic acid sample from the subject the presence of a 94A>C polymorphism in the inosine triphosphate pyrophosphatase (ITPA) gene, wherein the presence of said polymorphism is indicative of clinical responsiveness to said methotrexate therapy.

2. The method according to claim 1, wherein said methotrexate responsiveness is measured as a disease activity score (DAS) less than or equal to 2.4.

3. The method according to claim 1, wherein the polymorphism is detected by microarray analysis, DNA sequencing or allele specific PCR techniques.

4. The method of claim 1, further comprising selecting or adjusting said methotrexate therapy depending upon the results of said detecting.

5. The method of claim 4, wherein said selected or adjusted methotrexate therapy is methotrexate monotherapy, methotrexate combination therapy, or methotrexate biologic therapy.

6. The method of claim 1 further comprising detecting the presence of at least one polymorphism selected from the group consisting of a 34C>T polymorphism in the adenosine monophosphate deaminase (AMPD1) gene, a 2756A>G polymorphism in the methionine synthase (MTR) gene, and a 66A>G polymorphism in the methionine synthase reductase (MTRR) gene, wherein the presence of said polymorphisms is indicative of clinical responsiveness to said antifolate therapy.

* * * * *